(12) United States Patent
Binder et al.

(10) Patent No.: US 11,001,812 B2
(45) Date of Patent: May 11, 2021

(54) TRICHOTHECENE-TRANSFORMING ALCOHOL DEHYDROGENASE, METHOD FOR TRANSFORMING TRICHOTHECENES AND TRICHOTHECENE-TRANSFORMING ADDITIVE

(71) Applicant: Erber Aktiengesellschaft, Getzersdorf bei Traismauer (

TRICHOTHECENE-TRANSFORMING ALCOHOL DEHYDROGENASE, METHOD FOR TRANSFORMING TRICHOTHECENES AND TRICHOTHECENE-TRANSFORMING ADDITIVE

BACKGROUND OF THE INVENTION

The present invention refers to the use of a trichothecene-transforming alcohol dehydrogenase, a procedure for the transformation of trichothecenes, and a trichothecene-transforming additive.

Trichothecenes represent a frequently occurring group of mycotoxins that includes deoxynivalenol (DON, CAS no. 51481-10-8), T-2 toxin (CAS no. 21259-20-1), HT-2 toxin (CAS no. 26934-87-2), nivalenol (CAS no. 23282-20-4), fuseranon-X (CAS no. 23255-69-8), scripentriol, 15-acetoxyscirpenol (CAS no. 2623-22-5), 4,15-diacetoxyscirpenol (CAS no. 2270-40-8), trichodermol (CAS no. 2198-93-8), verrucarin A (CAS no. 3148-09-2), verrucarin J (CAS no. 4643-58-7), isotrichodermin (CAS no. 91423-90-4), hydroxyisotrichodermin (CAS no. 344781-02-8), calonectrin (CAS no. 38818-51-8), T-2 tetraol (CAS no. 34114-99-3), deacetylneosolaniol (CAS no. 74833-39-9), neosolaniol (CAS no. 36519-25-2), acetylneosolaniol (CAS no. 65041-92-1), sporotrichiol (CAS no. 101401-89-2), trichotriol (CAS no. 109890-37-1), sambucinol (CAS no. 90044-33-0), and culmorin (CAS no. 18374-83-9), among others. Trichothecenes, particularly DON, also known as vomitoxin, can be produced by a number of *Fusarium* fungi, especially *F. graminearum* and *F. culmorum*. These fungi attack crops such as maize, various types of grain, such as wheat, oats, or barley, whereas usually the fungal attack occurs before harvest and the fungal growth or mycotoxin formation can also occur before, or in the case of improper storage, after harvest.

The Food and Agriculture Organization (FAO) estimates that worldwide 25% of agricultural products are contaminated with mycotoxins, which results in considerable economic losses. In a more current study carried out worldwide by I. Rodrigues and K. Naehrer, Toxins, 2012, 4, 663-675, during a time period from January 2009 to December 2011, a total of 23,781 samples were analysed, of which 81% tested positive for at least one mycotoxin and 59% tested positive for trichothecenes, especially DON. Trichothecenes, especially DON could be found with a frequency of up to 100% in all regions of the world, as well as in all grain and feed classes tested, such as maize, soya meal, wheat, wheat bran, DDGS (distiller's dried grains with solubles), and in prepared feed mixtures. Apart from basic, non-processed foodstuffs, evidence of trichothecenes was also found in processed foods, such as flour, breakfast cereal, pasta products, bread, pastry, and wheat-based children's and baby food.

Trichothecenes have the following structural formula:

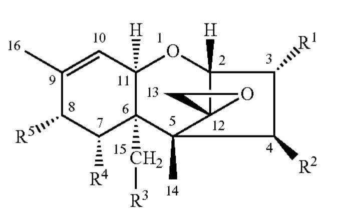

wherein the different substitution remainders R1 to R5 differ depending on the type of trichothecene. It is a known fact that, in addition to the epoxy group, an intact alpha-hydroxy group on the C-3 atom of the trichothecenes is jointly responsible for their toxic effect. Trichothecene types with a hydroxy group on the C-3 atom include deoxynivalenol, T-2 toxin, HT-2 toxin, nivalenol, fuseranon-X, 15-acetoxyscirpenol, 4,15-diacetoxyscirpenol, trichodermol, T-2 tetraol, deacetylneosolaniol, acetylneosolaniol, sporotrichiol, trichotriol, sambucinol, and culmorin.

Deoxynivalenol (DON) has a characteristic carbonyl group on the C-8 atom and has the following structural formula:

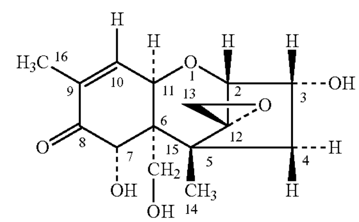

and the IUPAC name (3α,7α)-3,7,15-trihydroxy-12,13-epoxytrichothec-9-en-8-one. In nature, several toxic DON subtypes also occur with a hydroxy group on the C-3 atom. Examples of these are acetylated DON (e.g. 15 acyl DON), glycosylated DON, DON sulfonate (e.g. DONS-1, DONS-2), or DON sulfate (DON 15 sulfate). These DON subtypes also belong to the trichothecene types with a hydroxy group or substituted hydroxy group on the C-3 atom.

Because of the toxic effect of DON, limits or maximum levels have been defined by the competent authorities for food and feed. Thus the European Union has regulated the DON content in food (EC no. 1881/2006, EC no. 1126/2007) and has recommended maximum levels for feed (2006/576/EC). In the USA, the FDA has published maximum levels.

Illnesses that are caused by ingesting mycotoxins in humans or animals are referred to as mycotoxicoses. In the case of trichothecenes or trichothecene types, these are also referred to as "trichothecene mycotoxicoses", more specifically as "mycotoxicoses caused by trichothecenes exhibiting a hydroxyl group on the C-3 atom", or even more specifically as "DON mycotoxicoses". It is a known fact that the toxic effects of trichothecenes on animals and humans are based on several factors. These factors include the inhibition of protein biosynthesis, possible interaction with serotonin and dopamine receptors, and the upregulation of proinflammatory cytokines (EFSA Journal 2004, 73, 1-41). Moreover, DON mycotoxicoses cause changes in biomarkers, as diagnosed by an increase in the IgA concentration in blood, an increase in the SOCS3 concentration in the liver, or the reduction of IGFALS levels in the plasma (Pestka et al. 2004, Toxicol. Lett. 153, 61-73) as well as a reduction of the claudin concentration in the intestines (Pinton et al. 2009, Tox. Appl. Pharmacol. 237, 41-48).

For example, trichothecene mycotoxicoses are exhibited in swine by reduced feed intake, reduced growth, the occurrence of vomiting and diarrhea, as well as an immunological dysfunction and impaired nutrient absorption in the intestines. In the case of poultry, trichothecene mycotoxicoses cause a deterioration in feed intake, less weight gain, incidences of diarrhea, and a reduction in the weight of eggshells, among other things. In the case of ruminants, reduced feed intake and less milk production were described. In aquaculture, trichothecene mycotoxicoses cause a deterioration of feed intake and of growth rates in fish (e.g. salmon, catfish, or trout) and shrimp, among other things (Binder et. al, Guide to Mykotoxins; ISBN 978-0-9573721-0-8). Toxic effects have also been described in dogs and cats (EFSA Journal 2004, 73, 1-41). In humans, trichothecene mycotoxicoses can cause nausea, vomiting, diarrhea, abdominal pains, headache, or fever, among other things (Sobrova et. al, Interdisc. Toxicol. 2010, 3 (3), 94-99).

The primary strategy for the reduction of a trichothecene or DON contamination of food or feed is the restriction of fungal attack, for example, by complying with "good agricultural practice". This includes the use of seeds that are free of parasites and fungus, or the ploughing-in of crop residues. Moreover, fungal growth in the field can be reduced by the correct use of fungicides. After harvest, the crops should be stored at a residual humidity below 15% and at a low temperature to prevent fungal growth. Likewise, crops contaminated by fungal infestation should be removed before any further processing. Despite this list of measures, I. Rodriges and K. Naehrer reported (in 2012) that even in regions with the highest agricultural standards like the USA and Central Europe, 79% or 72% of all maize samples tested from 2009 to 2011 were contaminated with DON.

Other options for reducing mycotoxin contamination in food or feed are their adsorption or transformation. For adsorption, it is necessary for the binding of the mycotoxin to the adsorbent to be strong and specific over a wide pH range and that it remains stable in the gastrointestinal area during the entire digestion process. Although some non-biological adsorbents like activated carbon, silicates, or synthetic polymers like cholestyramine can be used efficiently for aflatoxins, their use for other mycotoxins, especially for trichothecenes, is not effective. Biological adsorbents such as yeast or yeast extracts are also described in the literature, but have a limitation similar to that of non-biological adsorbents. A substantial disadvantage of adsorbents is their possible non-specific bonding of other molecules that can be essential for nutrition.

Also the transformation, especially the detoxification of trichothecenes by physical and chemical treatments is limited because DON is very stable and remains stable even at heat treatments of up to 350° C.

A possible microbial transformation of DON was described in the EP-B 1 042 449, according to which the microorganism BBSH 797 (DSM 11798) is used for the detoxification of DON. Here the detoxification is based on the opening of the epoxide ring on the C-12 and C-13 atoms of DON. US 2012/0263827 A describes the biotransformation of DON to 3-epi-DON by a microorganism with the international Canadian accession number 040408-1. For many technical feed or food processes, however, an admixture of microorganisms or adsorbents is not possible, or is not legally permitted, so that there a transformation or a detoxification of trichothecenes like DON or DON subtypes is not possible.

Trichothecenes like DON and DON subtypes are absorbed rapidly into the gastrointestinal tract of human or animal bodies, which is why a fast and targeted detoxification is important.

The alcohol dehydrogenase of SEQ ID no. 1 was first described in the JP-A 2003/159079 for the production of 2-ketogulonic acid. WO 2009/133464 describes a process for the oxidation of saccharides by means of the enzyme of SEQ ID no. 1 in food and feed for the oxidation of starch, especially in the baking industry, to slow down the ageing processes in bread. Here, alcohol dehydrogenase is used for the oxidation of hydroxyl groups of carbohydrates.

Alcohol dehydrogenases with SEQ ID numbers 2 and 3 were identified in the course of a genome sequencing of *Devosia* sp. microorganisms and are stored online in the server of the National Center for Biotechnology Information (NCBI) under identification numbers GI:737041022 and GI:630002266. A more accurate characterisation of the alcohol dehydrogenases with SEQ ID numbers 2 and 3 was not given in the course of this work.

Because of the variety of toxic effects of trichothecenes and the frequency of their occurrence, there is therefore a need for substances or groups of substances like enzymes that can be used for the specific, safe, and permissible transformation, especially detoxification of trichothecenes.

BRIEF SUMMARY OF THE INVENTION

The present invention aims to use a specific alcohol dehydrogenase and variants thereof with which it is possible to transform at least one trichothecene exhibiting a hydroxyl group on the C-3 atom to less toxic products.

To solve the task, it has been surprisingly demonstrated that the use of an alcohol dehydrogenase of SEQ ID no. 1 containing metal ions and a quinone cofactor, or in addition, a functional variant exhibiting a sequence identity of at least 80%, preferably 86%, especially preferred at least 89% and at least one redox cofactor for the transformation of at least one trichothecene exhibiting a hydroxyl group on the C-3 atom enables it to transform trichothecenes exhibiting a hydroxyl group on the C-3 atom such as DON, T-2 toxin, or nivalenol specifically and reliably.

A transformation is understood to occur when the structure of toxins is changed wherein the toxins are preferably converted to non-toxic or less toxic metabolites, i.e., transformed. In the present case, a structural change occurs, especially on the C-3 atom of the trichothecenes exhibiting a hydroxyl group on the C-3 atom due to the catalytic conversion of the C-3 hydroxyl group to a keto group. Surprisingly, use of the alcohol dehydrogenase according to the invention produces a transformation of trichothecenes exhibiting a hydroxyl group on the C-3 atom, especially of DON, in the most diverse chemical and biological environments such as in buffer, feed mash, saliva, or feed containing gastric juices, or in intestinal contents containing feed. This is extraordinary because in the respective environments for enzymatic activity, important parameters such as the pH value, the protease concentration, ionic strength, or substance matrices are extremely different. As a result, an activity of the enzyme can be guaranteed from adding water to food and feed, to its oral intake and also in the mouth and gastrointestinal tract. It is surprising that for certain environments, an external addition of redox factors can be omitted; this applies in particular to feed mixtures, saliva, and gastric juices.

Alcohol dehydrogenase of SEQ ID no. 1 is a quinone cofactor-dependent alcohol dehydrogenase. To produce an active holoenzyme or an active alcohol dehydrogenase, a quinone cofactor, preferably pyrroloquinoline quinone (PCC) in the presence of a metal ion, preferably $Ca^{2+}$, can be bound to the enzyme. Therefore, the activated alcohol dehydrogenase contains both the quinone cofactor and the metal ion, wherein the molar ratio of enzyme to quinone cofactor is 1:1. Furthermore, a redox cofactor is required for the catalytic activity of the alcohol dehydrogenase, wherein either this is used in the form of a synthetically produced redox factor in addition to the activated alcohol dehydrogenase, or a redox factor also present in the food or feed and in secretions of animals or humans can be used. For example, these natural redox cofactors can be formed, and if necessary, extracted from food or feed in the course of the provision, processing, or digestion of the food or feed in the mouth and gastrointestinal tract of humans or animals. Examples of human or animal secretions that contain such a natural redox cofactor are digestion secretions such as saliva, gastric juice, intestinal juice, pancreatic fluid, bile, or rumen fluid.

The expressions "polypeptide variant" or "variant" refer to functional polypeptides that, compared to SEQ ID no. 1, at least have an amino acid substitution, wherein the enzymatic function is retained. The transformation, especially the oxidation of the hydroxyl group on the C-3 atom of trichothecenes to a keto group, is understood as an enzymatic function. Furthermore, a "polypeptide variant" can also have amino acid insertions or deletions, especially a C or N terminal extended or shortened sequence relative to the polypeptide sequence of the SEQ ID no. 1. An enzymatic function is then "essentially retained" if the enzymatic reaction mechanism remains unchanged, i.e., the trichothecene is oxidised in the same place and the enzymatic activity of the variant is at least 10%, preferably at least 50%, more preferably at least 90%, especially >100% based on the original, parental polypeptide of the SEQ ID no. 1.

The name "sequence identity" refers to a percent sequence identity. For amino acid sequences and nucleotide sequences, the sequence identity can be determined visually, but preferably calculated by a computer program. The amino acid sequence of SEQ ID no. 1 is defined as a reference sequence. The sequence comparison is also performed within sequence segments, in which case a segment is understood to be a continuous sequence of the reference sequence. The length of the sequence segments for peptide sequences is normally 3 to 200, preferably 15 to 65, most preferably 30 to 50 amino acids. There are many bioinformatics programs available for sale or free that can be used to determine the homology and that are continuously being further embodied. Examples of this are: GCG Wisconsin BestFit package (Devereux et al. 1984), BLAST (Altschul et al. 1990) or BLAST 2 (Tatusova and Madden 1999). Because of the different setting options for these algorithms, it is possible for them to arrive at different results for the same input sequences. Therefore, the search algorithm and the associated setting must be defined. In the present case, the NCBI BLAST (Basic Local Alignment Search Tool) program, especially with BLASTP for polypeptides, which is available from the homepage of the "National Center for Biotechnology Information" (NCBI, http://www.ncbi.nlm.nih.gov/) was used to calculate the sequence identity. This way it is possible to compare two or more sequences with each other according to the algorithm of Altschul et al., 1997 (Nucleic Acids Res., 25:3389-3402). Here, the program versions of 12 Aug. 2014 were used. The basic settings were used as program settings, especially for the amino acid comparison: "max target sequence"=100; "expected threshold"=10; "word size"=3; "matrix"=BLOSOM62; "gap costs"="existence: 11; extension: 1"; "computational adjustment"="conditional compositional score matrix adjustment".

By using an alcohol dehydrogenase containing metal ions and a quinone cofactor according to the invention or a functional variant thereof, it is possible to transform at least 20%, preferably at least 50%, especially at least 90% of at least one trichothecene exhibiting a hydroxyl group on the C-3 atom, especially DON, wherein it is sufficient to bring an alcohol dehydrogenase containing metal ions and a quinone cofactor or a functional variant thereof into contact with at least one trichothecene exhibiting a hydroxyl group on the C-3 atom for at least one minute, preferably at least 5 minutes, especially at least 60 minutes.

According to a further embodiment of the invention, the amino acid sequence of the functional variant selected from the group of SEQ ID numbers 2 to 4 is used. With these functional variants that have a sequence identity of at least 86% for the alcohol dehydrogenase of SEQ ID no. 1, it is possible to transform trichothecenes exhibiting a hydroxyl group on the C-3 atom, especially DON, with consistently good results.

According to a further embodiment of the invention, the quinone cofactor selected from the group PCC, TTC, TPC, LTC, and CTC, preferably PCC, was used. By using one of the quinone cofactors pyrroloquinoline quinone (PCC, CAS no. 72909-34-3), tryptophan tryptophylquinone (TTQ, CAS no. 134645-25-3), topaquinone (TPC, CAS no. 64192-68-3), lysine tyrosylquinone (LTQ, CAS no. 178989-72-5) or cysteine tryptophylquinone (CTC, CAS no. 400616-72-0) in the alcohol dehydrogenases, it is possible to transform trichothecenes exhibiting a hydroxyl group on the C-3 atom, like DON, to derivatives that are either non-toxic or harmless from a toxicological standpoint.

An especially fast and complete binding of the quinone cofactor to the alcohol dehydrogenase is achieved by being bound by at least one of the metal ions selected from the group $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^{2+}$, $Cu^{3+}$, $Co^{2+}$ and $Co^3$, preferably $Ca^{2+}$ and $Mg^{2+}$.

By also using at least one redox cofactor selected from the phenazine methosulphate group (PMS), PMS derivatives, potassium hexacyanoferrate (III), sodium hexacyanoferrate (III), cytochrome C, coenzyme Q1, coenzyme Q10, methylene blue and N,N,N',N'-tetramethyl-p-phenylenediamine (TMPD), preferably phenazine methosulphate (PMS, CAS no.: 299-11-6), coenzyme Q1 and coenzyme Q10, a complete and fast transformation of the trichothecenes is possible exclusively in the presence of moisture, so as to ensure that trichothecenes contained in feed components are already transformed to non-toxic derivatives during the production of feed and in any case prior to being used with animals, for example. Examples of PMS derivatives are: 1-hydroxyphenazine, 2-(pentaprenyloxy)dihydrophenazine, 5,10-dihydro-9-dimethylallylphenazine-1-carboxylic acid, 5,10-dihydrophenazine-1-carboxylic acid, 5-methylphenazinium methyl sulfate, 6-acetophenazine-1-carboxylic acid, benthophoenin, clofazimine, dihydromethanophenazine, esmeraldic acid, esmeraldin B, izumiphenazine A-C, Janus Green B cation, methanophenazine pelagiomicin A, phenazine, phenazine-1,6-dicarboxylic acid, phenazine-1-carboxamide, phenazine-1-carboxylic acid, phenosafranine, pyocyanin, saphenamycin, or saphenic acid methyl ester. Because of the transformation of trichothecenes exhibiting a hydroxyl group on the C-3 atom in food and feed, especially feed for swine, poultry, cattle, horses, fish, aquaculture, and domestic animals and in plant-based raw materials used for the production or processing of food and feed, it is possible to prevent harm to the health of animals and humans by use according to the invention.

Furthermore, the present invention aims to provide a procedure with which it is possible to transform trichothecenes, especially trichothecenes exhibiting a hydroxyl group on the C-3 atom, safely and reliably to less toxic products, regardless of whether the agricultural products in which they are present have been processed or not.

To solve this task, the procedure according to the invention for the enzymatic transformation of trichothecenes is essentially characterised by at least one trichothecene exhibiting a hydroxyl group on the C-3 atom being brought into contact with an alcohol dehydrogenase of SEQ ID no. 1 containing metal ions and a quinone cofactor, or with a functional variant additionally exhibiting a sequence identity of at least 80%, preferably at least 86%, especially preferred at least 89% with at least one redox cofactor and water, and if necessary at least one excipient. By bringing a trichothecene exhibiting a hydroxyl group on the C-3 atom into contact with an alcohol dehydrogenase of SEQ ID no. 1 containing metal ions and a quinone cofactor, and in addition, at least one redox cofactor and water, it is possible to oxidise the hydroxyl group present on the C-3 atom of the trichothecenes to a ketone, in which case the trichothecene as such is detoxified and is transformed to a non-toxic or low-toxicity compound.

By continuing to use a function variant of the amino acid sequence selected from the group of SEQ ID numbers 2 to 4 instead of the amino acid sequence of SEQ ID no. 1, the identical advantages that are achieved by using alcohol dehydrogenase of SEQ ID no. 1 can be achieved, and a transformation of the trichothecenes contained in food and feed can be achieved particularly fast and reliably, regardless of their processing status, i.e., regardless of whether they are already processed agricultural products or not.

A particularly fast and complete transformation of a trichothecene exhibiting a hydroxyl group on the C-3 atom is achieved with the procedure according to the invention at a temperature between 5° C. and 55° C., preferably between 10° C. and 50° C., especially preferred between 28° C. and 45° C. Because the procedure according to the invention can be performed in such a broad temperature range, alcohol dehydrogenase of SEQ ID no. 1 or its functional variants that exhibit a sequence of at least 80% of SEQ ID no. 1 can be used in the most diverse applications such as aquaculture or also technological processes at elevated temperatures. Examples of such technological processes in which a transformation of trichothecenes at elevated temperatures is important would be procedures for processing feed, the production of pasta and other maize products like polenta, popcorn, corn flakes, cornbread or tortillas, as well as liquefaction processes of stark, saccharification processes, or fermentation processes such as mashing or fermentation processes, especially bioethanol production. Here it is important to ensure that the food or feed produced by these processes does not contain any harmful quantities of trichothecenes exhibiting a hydroxyl group on the C-3 atom.

According to a further embodiment of the procedure according to the invention, this is conducted in such a way that at least one trichothecene exhibiting a hydroxyl group on the C-3 atom is brought into contact with the alcohol dehydrogenase containing metal ions and a quinone cofactor, or at least a functional variant thereof, with the redox factor, with water, and if necessary, with the excipient, for at least one minute, preferably for at least 5 minutes, especially preferred for at least 60 minutes. Because contact times between 1 minute and more than 60 minutes are sufficient to achieve adequate transformation of the trichothecenes to non-toxic or low-toxicity derivatives, the procedure according to the invention can be used in a procedure for processing basic agricultural materials for food or feed, for example. On the other hand, it can also be administered by the farmer immediately prior to feeding, for example, by adding water to the feed and letting it stand between 1 minute and up to approximately 1 hour at a temperature between 5° C. and 55° C., which will initiate a transformation of the trichothecenes to non-toxic products.

A particularly fast and complete transformation is possible if the quinone cofactor is selected from the group PCC, TTC, PTC, LTC and CTC, preferably PCC, as this corresponds to a further embodiment of the procedure according to the invention. Such a quinone cofactor allows the alcohol dehydrogenases to attack the hydroxyl group on the C-3 atom of the trichothecenes fast and reliably and to transform it to a keto group containing the non-toxic derivative.

A further completion of the reaction and in particular an acceleration of the reaction are possible if the cofactor in the procedure according to the invention is bound to the alcohol dehydrogenase by means of at least one metal ion selected from the group $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^{2+}$, $Cu^{3+}$, $Co^{2+}$ and $Co^{3+}$, preferably $Ca^{2+}$ and $Mg^{2+}$. Performing the procedure in such a manner produces not only a strong binding of the quinone cofactor to the alcohol dehydrogenase, but also allows a fast and reliable transformation of trichothecenes.

For a further improvement of the transformation of the trichothecenes, especially for a completion of the transformation reaction, the procedure according to the invention is continued so that a redox factor selected from the group PMS, PMS derivatives, potassium hexacyanoferrate (III), sodium hexacyanoferrate (III), cytochrome C, coenzyme Q1, coenzyme Q10, methylene blue, and TMPD, preferably PMS, coenzyme Q1 and coenzyme Q10, is used. By adding such a redox cofactor it is possible to perform the transformation of the trichothecenes exhibiting a hydroxyl group on the C-3 atom in an aqueous medium, for example, such as in feed slurry or feed that is administered to animals in aquaculture, without the redox factors, which could be obtained from saliva, gastric juice or intestinal juice, for example, having to be added or having to be present, or the animal having to already have ingested the feed slurry or the feed, in which case a resorption of trichothecenes by the animals ingesting the feed can be prevented.

Finally, the invention aims to provide a trichothecene-transforming additive with which it is possible to transform trichothecenes in feed or food safely and reliably to non-toxic derivatives.

To solve this task, the additive according to the invention is essentially characterised in that it contains an alcohol dehydrogenase of SEQ ID no. 1 containing metal ions and a quinone cofactor, or a functional variant additionally exhibiting a sequence identity of at least 80%, preferably at least 86%, especially preferred at least 89%, and if necessary, additionally at least one additional component selected from the group consisting of a synthetic redox cofactor and at least one excipient. Such additives can be mixed with conventional feeds in low concentrations, for example, approximately 10 g to 1 kg to a tonne of feed, and in such a low concentration, allow trichothecenes exhibiting a hydroxyl group on the C-3 atom to be transformed to non-toxic derivatives so that altogether the health and performance capabilities of animals that are fed with this feed, for example, will improve and thus, not only the failure rates will be able to be reduced, but also the feed utilisation will be improved.

Consistently good results can be achieved with an additive according to the invention that, instead of the alcohol dehydrogenase of SEQ ID no. 1, contains a functional variant of the same, selected from the group of SEQ ID numbers 2 to 4.

For an essentially complete transformation of the hydroxyl group present on the C-3 atom of trichothecenes by the additive according to the invention, it is further embodied to contain a quinone cofactor selected from the group PCC, TTC, TPC, LTC, and CTC, as well as a metal ion selected from the group $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^{2+}$, $Cu^{3+}$, $Co^{2+}$ and $Co^{3+}$. With such a further embodiment, on the one hand it is possible to bind the quinone cofactor safely and reliably to the alcohol dehydrogenase, and on the other hand, with an alcohol dehydrogenase that contains such supplements, a complete transformation of trichothecenes like deoxynivalenol that exhibit a hydroxyl group on the C-3 atom of the molecule can be achieved.

In order for such a reaction to be carried out as well without the presence of redox cofactors such as those occurring naturally in saliva, gastric juice, or intestinal juice or the like, the additive according to the invention is further embodied so that in addition, as a further redox cofactor, a synthetic redox cofactor is additionally selected from the group PMS, PMS derivatives, potassium hexacyanoferrate (III), sodium hexacyanoferrate (III), cytochrome C, coenzyme Q1, coenzyme Q10, methylene blue, and TMPD, preferably PMS, coenzyme Q1 and coenzyme Q10.

According to a further embodiment of the invention, the additive is developed so that the excipient is selected from a group of inert carriers, vitamins, mineral substances, phytogenetic substances, enzymes and additional components for the detoxification of mycotoxins like mycotoxin-degrading enzymes, especially aflatoxin-oxidases, ergotamine hydrolases, ergotamine amidases, zearalenone esterases, zearalenone lactonases, zearalenone hydrolases, ochratoxin amidases, fumonisin aminotransferases, fumonisin carboxyltransferases, amino polyol amine oxidases, deoxynivalenol epoxide hydrolases, deoxynivalenol dehydrogenases, deoxynivalenol oxidases, trichothecene dehydrogenases, trichothecene oxidases; and mycotoxin-transforming microorganisms such as DSM 11798; and mycotoxin-binding substances such as microbial cell walls or inorganic materials like bentonite or smectite. For example, the use of such an additive can ensure that any quantities of trichothecenes exhibiting a hydroxyl group on the C-3 atom that may be contained in feed or food as well as any additional mycotoxins such as *Fusarium* toxins, ergotamines, ochratoxins, are detoxified with certainty to the extent that a harmful effect of the mycotoxin on the organism of the subject ingesting this feed or food is absent.

Further applications for the invention are additives that, in addition to at least one alcohol dehydrogenase according to the invention, additionally contain at least one enzyme that is involved in the breakdown of proteins, for example, such as proteases, or that are involved in the metabolism of starch or fibre or fat or glycogen, such as amylase, cellulase or glucanase, and for example, hydrolases, liptolytic enzymes, mannosidases, oxidases, oxidoreductases, phytases or xylanases.

It goes without saying that the additive can of course be present in encapsulated or coated form, in which case, standard methods such as those described in WO 92/12645 can be used. By encapsulating or coating, it is possible to transport the additive to the location where it is to be used without modification, especially without any degradation or damage, so that the polypeptide starts to take effect only after the shell is dissolved, as in the digestive tract of animals, for example, which can achieve an even more targeted, faster and more complete breakdown of the trichothecenes exhibiting a hydroxyl group on the C-3 atom, even in an acidic, protease-rich, and anaerobic environment. Furthermore, by encapsulating or coating, it is also possible to increase the temperature stability of the alcohol dehydrogenases in the additive, in which case its use in the pelleting process for feed is improved, for example.

The additive according to the invention can be used in a wide variety of applications, such as the production of a compound, for the prevention and/or treatment of trichothecene mycotoxicoses, preferably of mycotoxicoses caused by trichothecenes that exhibit a hydroxyl group on the C-3 atom, especially such as deoxynivalenol mycotoxicoses. Such mycotoxicoses have serious consequences for humans and animals. By such use of the additive, in the case of a prophylaxis, it is possible to maintain the state of health of humans and animals essentially at the same level as without or with a reduced oral intake of the toxins, despite an oral intake of trichothecenes, especially of trichothecenes exhibiting a hydroxyl group on the C-3 atom, especially deoxynivalenol. In the case of the treatment of mycotoxicoses, it is possible to relieve the symptoms of such a disease, and in particular to normalise the SOCS3 concentration in the liver or the IGFALS levels in the plasma as well as the claudin concentration in the intestines.

Moreover, it is possible by such use to improve the productivity of livestock, especially feed utilisation and weight increase, and to lower the mortality rate.

BRIEF DESCRIPTION OF THE DRAWINGS

The invention is explained below based on embodiments and a drawing. Herein.

DETAILED DESCRIPTION OF THE INVENTION

Figure 1:
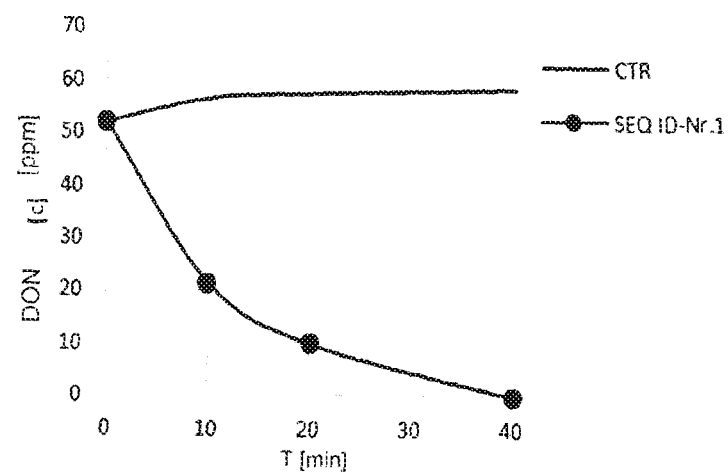
FIG. 1 shows the chronological transformation of deoxynivalenol for the activated alcohol dehydrogenase of SEQ ID no. 1 as well as a check (CTR) as a comparison.

Example 1: Cloning of the Genes and Purification of the Alcohol Dehydrogenase

The codon-optimised nucleotide sequences of the alcohol dehydrogenase of SEQ ID numbers 1 to 4 for the respective host cell were taken from DNA2.0 and contained restriction sites at the nucleic acid level on the 5' end and on the 3' end of the sequence, and at the amino acid level, additionally a C- or N-terminal 6×His tag. These nucleotide sequences were integrated by means of standard methods in expression vectors for the expression in *Escherichia coli* or *Komagataella pastoris*, and transformed to *E. coli* or *K. pastoris*, and expressed in *E. coli* or *K. pastoris* (J. M. Cregg, Pichia Protocols, second Edition, ISBN-10: 1588294293, 2007; J. Sambrook et al. 2012, Molecular Cloning, A Laboratory Manual 4th Edition, Cold Spring Harbor).

The alcohol dehydrogenases with SEQ ID numbers 1 to 4 were selectively fortified chromatographically from cell lysates in the case of the expression in *E. coli* and from the intercellular expression in *K. pastoris* or from the culture supernatant in the case of the extracellular expression in *K. pastoris* by means of standard methods via nickel sepharose columns. The selectively fortified eluates were incubated and activated in the presence of metal ions and quinone cofactors, in which case "activated" means that the alcohol dehydrogenases exhibit both the metal ion and the quinone cofactor as bound. These activated alcohol dehydrogenases were used to determine the enzymatic properties of the alcohol dehydrogenases with SEQ ID numbers 1 to 4 in examples 3 to 7 below. The total protein concentration was determined photometrically with the Bradford reagent (Sigma #B6916), in which case the absorptions were measured in a microplate photometer (plate reader, Biotek, Synergy HT) at a wavelength of 595 nm. The protein concentration was ascertained based on a calibration curve that was determined using the Bradford assay by measuring the bovine serum albumin (BSA, Sigma #A4919) solutions with concentrations up to a maximum of 1500 µg/ml.

Example 2: Determination of the Sequence Identity

The percent sequence identity over the entire length of the amino acid sequence of the alcohol dehydrogenases with SEQ ID numbers 1-4 relative to each other was determined using the BLAST program (Basic Local Alignment Search Tool), especially BLASTP, which is available for use on the homepage of the National Center for Biotechnology Information (NCBI; http://www.ncbi.nlm.nih.gov/), with which it is possible to compare two or more sequences with each other according to the algorithm by Altschul et al., 1997 (Nucleic Acids Res. (1997) 25:3389-3402). The basic settings were used as program settings, especially: "max target sequence"=100; "expected threshold"=10; "word size"=3; "matrix"=BLOSOM62; "gap costs"="existence: 11; extension: 1"; "computational adjustment"="conditional compositional score matrix adjustment". The percentage identities of the amino acid sequences to one another are shown in Table 1:

TABLE 1

|  | SEQ ID no. 1 | SEQ ID no. 2 | SEQ ID no. 3 | SEQ ID no. 4 |
|---|---|---|---|---|
| SEQ ID no. 1 | 100% | 87% | 89% | 86% |
| SEQ ID no. 2 | 87% | 100% | 99% | 90% |
| SEQ ID no. 3 | 89% | 99% | 100% | 91% |
| SEQ ID no. 4 | 86% | 90% | 91% | 100% |

Example 3: Transformation of Trichothecene Exhibiting a Hydroxyl Group on the C-3 Atom To determine their suitability to transform trichothecenes that exhibit a hydroxyl group on the C-3 atom, especially DON, nivalenol and T-2 toxin, the alcohol dehydrogenases with SEQ ID numbers 1-4 were produced with a C-terminal 6×His tag in *E. coli*, as described in Example 1.

A transformation is then present when the quantity of the trichothecene exhibiting a hydroxyl group on the C-3 atom is reduced by bringing it into contact with an activated alcohol dehydrogenase, i.e., an alcohol dehydrogenase that contains metal ions and a quinone cofactor.

In each case, 100 ml of an *E. coli* culture with an optical density (OD600 nm) of 2.0-2.5 were harvested by centrifugation at 4° C. and resuspended in 20 ml potassium phosphate buffer. The cell suspensions were lysed by French press treatment 3 times at 20,000 psi. The cell lysates were separated into soluble and insoluble parts by centrifugation. The supernatant was filtered sterilely and the alcohol dehydrogenase was fortified by means of standard methods via nickel sepharose columns. Following this, a buffer exchange was performed by dialysis with specific tubes with a cut-off of ten kilodaltons. The resulting total protein concentration was measured by Bradford assay.

The quinone cofactors and the metal ions were bound to the alcohol dehydrogenase by incubation in an aqueous solution. Here, the quinone cofactor, such as pyrroloquinoline quinone (PCC, CAS no. 72909-34-3), tryptophan tryptophylquinone (TTC, CAS no. 134645-25-3), topaquinone (TPC, CAS no. 64192-68-3), lysine tyrosylquinone (LTC, CAS no. 178989-72-5) and cysteine tryptophylquinone (CTC, CAS no. 400616-72-0), is added to the existing total protein concentration as an aqueous solution in an approximately twentyfold molar excess. The metal ions selected from $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^2$, $Cu^{3+}$, $Co^{2+}$ and $Co^{3+}$ are used as an aqueous solution of a salt thereof. Unless otherwise indicated, the alcohol dehydrogenases were normally used with PCC (Sigma Aldrich #D7783) and $Ca^{2+}$, activated as a 5 mM $CaCl_2$ solution. The enzymes purified and activated in this manner were used for in vitro transformation assays of a trichothecene exhibiting a hydroxyl group on the C-3 atom. Unless otherwise indicated, the terms "enzyme or "alcohol dehydrogenase" are always understood to refer to the appropriately activated alcohol dehydrogenases containing metal ions and a quinone cofactor.

The transformation assays were carried out in an aqueous solution with the following components: 100 mM Tris-HCl pH 7.5 or 10% Teorell Stenhagen pH 7.5; synthetic redox cofactor selected from group 1 mM phenazine methosulphate PMS (Sigma Aldrich #P9625), 1 mM methylene blue (Sigma #M9140), 1 mM coenzyme Q10 (Sigma #C9538), 1 mM coenzyme Q1 (Sigma #C9538) and 20 mM potassium hexacyanoferrate (111) PFC (111) (Fluke #60300); 10 ppm up to a maximum of 100 ppm of a trichothecene exhibiting a hydroxyl group on the C-3 atom by adding the desired quantity of a toxin substrate stock solution; and 10 nM to 100 nM, maximum 300 nM of an activated alcohol dehydrogenases of SEQ ID no. 1, 2, 3 or 4 containing metal ions and a quinone cofactor. Unless otherwise indicated, the Tris-HCl buffer, the redox cofactor PMS, DON and the alcohol dehydrogenase of SEQ ID no. 1 are normally used. Each transformation assay was carried out in a 1.5 ml brown Eppendorf reaction vessel. The reaction mixtures were incubated at 30° C. in a thermoblock for up to 120 minutes, at least 40 minutes. After 0, 10, 20, 30, and 40 minutes, a sample of 0.1 ml was taken in each case and mixed with 0.1 ml methanol and stored at −20° C., or alternatively analysed immediately by LC-MS/MS or HPLC.

A sterilely filtered, aqueous 2000 ppm DON solution was used as the DON substrate stock solution. To produce this solution, DON in crystalline form (Biopure Standard from Romer Labs, art. no. 001050, pureness at least 98%) was weighed and dissolved. To quantify the trichothecenes exhibiting a hydroxyl group on the C-3 atom and their transformation metabolites, HPLC analyses were performed, wherein the substances were separated chromatographically by means of a Phenomenex C18 Gemini NX column with dimensions of 150 mm×4.6 mm and a particulate size of 5 μm. A methanol/water mixture with an ammonium acetate concentration of 5 mM was used as the eluant. The UV signal was recorded and evaluated at 220 nm. For the quantification by means of LC-MS/MS analyses, the substances were separated chromatographically by means of a Zorbax eclipse C8 column with dimensions of 150 mm×4.6 mm and a particulate size of 5 μm. A methanol/water mixture with an ammonium acetate concentration of 5 mM was used as the eluant. The UV signal at 220 nm was recorded. Electrospray ionisation (ESI) was used as the ionisation source. The trichothecenes exhibiting a hydroxyl group on the C-3 atom were quantified by means of a QTrap/LC/MS/MS (triple quadrupole, applied biosystems) in "enhanced mode".

Figure 2:
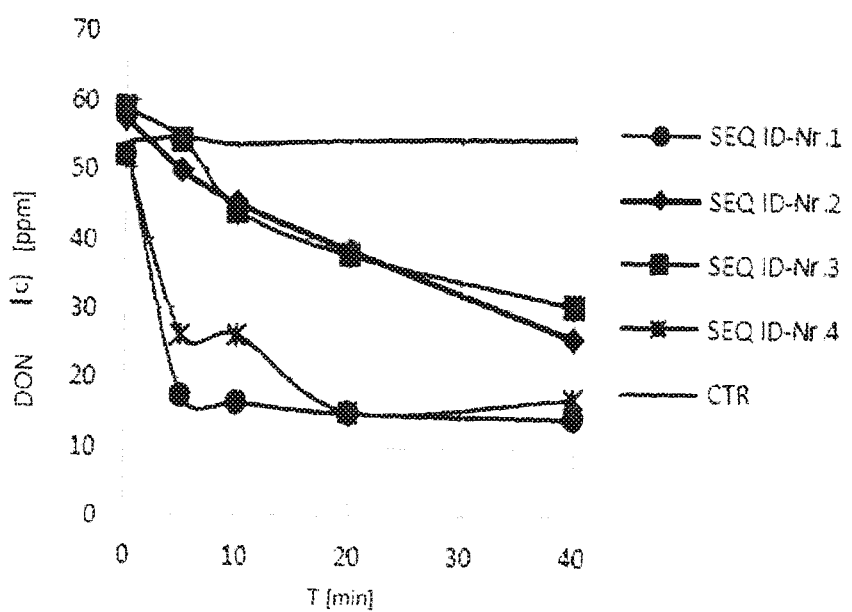
FIG. 2 shows the representation of the chronological transformation of DON with the activated alcohol dehydrogenase of SEQ ID numbers 1 to 4 as well as a check (CTR) as a comparison.

The negative slope of the transformation lines (=reduction in the toxin concentration over time) in the linear range were used as a standard for the activity of the alcohol dehydrogenases. To determine the residual activities, the measured activities for different parameters relative to the basic activity, measured under standard conditions, especially 30° C. and pH 7.5, were applied and usually represented as percentages. FIG. 1 shows the chronological transformation of DON for the activated alcohol dehydrogenase of SEQ ID no. 1 and FIG. 2 shows the activated alcohol dehydrogenases of SEQ ID numbers 2-4. From the illustrations it is clearly evident that a transformation of DON occurs because the concentration of DON was reduced based on the reality time.

FIG. 1 shows the transformation of DON with the alcohol dehydrogenase of SEQ ID no. 1 in 100 mM Tris HCl pH 7.5 in the presence of 50 ppm DON and 1 mM PMS. The measurement results were obtained by LC-MS/MS analyses (A) and the transformation of DON with the alcohol dehydrogenases of SEQ ID numbers 1-4 is shown in FIG. 2. The measurement results were obtained by HPLC analyses (B). CTR was used in the tests as a negative check that contained all the components of the transformation assay up to the alcohol dehydrogenases of SEQ ID numbers 1-4.

To compare the efficiency of the quinone cofactors, in the transformation assays, 10 nM of the alcohol dehydrogenase of SEQ ID no. 1 activated with quinone cofactors PCC, TTC, TPC, LTC, and CTC, 10 ppm DON, and 1 mM synthetic redox factor PMS each were mixed in 100 mM Tris-HCl pH 7.5 and incubated at 30° C. The DON concentrations were determined by means of LC-MS/MS after 30 minutes. The results are shown in Table 2.

To compare the efficiency of the redox cofactors, in the transformation assays, 10 nM activated enzyme (alcohol dehydrogenase of SEQ ID no. 1), 10 ppm DON, and 1 mM or 20 mM of the synthetic redox cofactors to be tested respectively were mixed in 100 mM Tris-HCl pH 7.5 and incubated at 30° C. The DON concentrations were determined by LC-MS/MS after 30 minutes. The results are shown in Table 2.

TABLE 2

| Quinone cofactor | DON [ppm] | Redox cofactor | DON [ppm] |
|---|---|---|---|
| PCC | 1.94 | 1 mM PMS | 1.95 |
| TTQ | 2.32 | 20 mM PFC (III) | 2.11 |
| TPQ | 2.41 | 1 mM coenzyme Q1 | 8.58 |
| LTQ | 2.04 | 1 mM methylene blue | 6.88 |

To test the influence of the metal ions in the activated enzyme on the transformation, the alcohol dehydrogenase of SEQ ID no. 1 and PCC were activated, but with different metal ions in each case, namely, $Mg^{2+}$, $Ca^{2+}$, $Zn^{2+}$, $Mn^{2+}$, $Fe^{2+}$ and $Cu^{2+}$. The transformation assays contained 10 nM activated alcohol dehydrogenase, 10 ppm DON, and 1 mM PMS in 100 mM Tris-HCl pH 7.5 respectively, and were incubated at 30° C. The DON concentrations were determined by means of LC-MS/MS after 30 minutes. The results are shown in Table 3.

TABLE 3

| Metal ion | DON [ppm] | Metal ion | DON [ppm] |
|---|---|---|---|
| $Mg^{2+}$ | 1.90 | $Mn^{2+}$ | 2.57 |
| $Ca^{2+}$ | 1.98 | $Fe^{2+}$ | 2.17 |
| $Zn^{2+}$ | 2.46 | $Cu^{2+}$ | 2.61 |

Analogously to the above-mentioned DON transformation assays, transformation assays were carried out with other trichothecenes exhibiting a hydroxyl group on the C-3 atom. In these assays, instead of 50 ppm DON, 50 ppm T-2 toxin or 50 ppm nivalenol were used. All four alcohol dehydrogenases of SEQ ID numbers 1 to 4 containing metal ions and a quinone cofactor were also able to transform T-2 toxin and nivalenol, in which case, more than half the originally used toxin was transformed within 30 minutes.

Example 4: Measurement of the Activity Areas

To determine the capacity of alcohol dehydrogenases of SEQ ID numbers 1-4 to transform DON under different conditions, alcohol dehydrogenase of SEQ ID no. 1 was used as an example.

The alcohol dehydrogenase of SEQ ID no. 1 was produced and activated with $Ca^{2+}$ and PCC as described in Example 3. To determine the activity of the enzyme over a temperature range from 10° C. to 50° C. and over a pH range from 3.0 to 9.0, a 10% Teorell Stenhagen buffer was used instead of the 100 mM Tris-HCl pH 7.5 buffer.

The transformation assays to determine the activities at different temperatures were carried out in an aqueous solution with the following components: 10% Teorell Stenhagen pH 7.5, 1 mM synthetic redox cofactor PMS, 50 ppm DON, and 10 nM activated alcohol dehydrogenases of SEQ ID no. 1. The transformation assays were incubated up to 60 min in a thermocycler (Eppendorf) with a temperature gradient from 10° C. to 50° C. After 0, 10, 20, 30, 40, and 60 minutes, a sample of 0.05 ml was taken in each case and mixed with 0.05 ml methanol to stop the reaction, and stored at −20° C. The samples were prepared for the LC-MS/MS, as described in Example 3, and analysed by means of LC-MS/MS. The course of the DON reduction was determined for each temperature and the activity was calculated, as described in Example 3. The slope of the linear range of the transformation line at 30° C. was used as a reference value to calculate the residual activity at the other temperatures. Table 4 shows the temperatures in ° C. and the associated residual activities in percent. Surprisingly, it has been shown that the alcohol dehydrogenase of SEQ ID no. 1 is active over a broad temperature range. At 10° C., a residual activity of 48% was measured, and at approximately 50° C., a residual activity of 67%.

TABLE 4

| Temperature [° C.] | Residual activity [%] | Temperature [° C.] | Residual activity [%] |
|---|---|---|---|
| 10.0 | 48 | 32.8 | 105 |
| 12.7 | 60 | 33 | 108 |
| 15 | 69 | 35.3 | 105 |
| 17.6 | 73 | 38.4 | 120 |
| 20.5 | 86 | 40.7 | 116 |
| 23.3 | 89 | 43.2 | 108 |
| 26.2 | 82 | 45.9 | 96 |
| 28.3 | 100 | 48.2 | 89 |
| 30.2 | 100 | 49.8 | 67 |

The transformation assays to determine the activity in a pH range from 4.0 to 9.0 were carried out in an aqueous solution with the following components: 10% Teorell Stenhagen pH 4.0 to pH 10.0, 20 mM synthetic redox cofactor PFC, 100 ppm DON, and 20 nM activated alcohol dehydrogenases of SEQ ID no. 1. The transformation assays were incubated up to 60 min in a thermocycler at 30° C. After 0, 10, 20, 30, 40 and 60 minutes, a sample of 0.05 ml was taken in each case and mixed with 0.05 ml methanol to stop the reaction, and stored at −20° C. As described in Example 3, the samples were diluted and analysed by means of LC-MS/MS. The course of the DON reduction was determined at each pH value and the activity was calculated, as described in Example 3. The slope of the linear range of the transformation line at pH 7.5 was used as a reference value to calculate the residual activity at the other temperatures. Table 5 shows the pH values and the associated residual activities (DON reduction based on the reference pH value of 7.5) in percent.

TABLE 5

| pH | Residual activity |
|---|---|
| 4.0 | 10% |
| 5.0 | 18% |
| 6.0 | 20% |
| 6.5 | 52% |
| 7.0 | 105% |
| 7.5 | 100% |
| 8.0 | 69% |
| 9.0 | 105% |

Example 5: Determining the Temperature Stability

The temperature stability of the alcohol dehydrogenase of SEQ ID no. 1 was determined over a range from 30° C. to 55° C. To do this, the activated alcohol dehydrogenase was incubated in a 100 mM Tris-HCl buffer, pH 7.5 for up to 60 min at a specific temperature in a thermocycler (Eppendorf). After 0, 5, 10, 15, 20, 30, 40, and 60 minutes, an aliquot of the alcohol dehydrogenase was taken and the activity was determined in a DON transformation assay, as described in Example 3. The transformation assays contained the following components: 100 mM Tris-HCl, pH 7.5, 1 mM PMS, 50 ppm DON, 10 nM activated alcohol dehydrogenases of SEQ ID no. 1. As described in Example 3, the reactions were incubated and the sampling to determine the activity was done after 0, 10, 20, 30, 40 and 60 min. The course of the DON reduction was determined for each temperature for each incubation time. The slope of the linear range of the DON transformation line was calculated to determine the temperature stability. The slope of the linear range of the DON transformation line of the respective temperature at the time of t=0 min was used as the reference value for the calculation of the residual activities. Table 6 shows the temperatures in ° C., the incubation time in minutes, and the associated residual activities in percent. The alcohol dehydrogenase of SEQ ID no. 1 was the steadiest when stored for an hour at temperatures of 30° C. and 37° C. In comparison to this, the alcohol dehydrogenase still had 73% residual activity at 40° C. after being stored an hour. A 50% residual activity was measured after being stored at 45° C. for 30 min. Surprisingly, a residual activity of 84% was detected after being stored 5 min at 50° C.

TABLE 6

| | Incubation time | | | | | | | |
|---|---|---|---|---|---|---|---|---|
| | 0 min | 5 min | 10 min | 15 min | 20 min | 30 min | 40 min | 60 min |
| 30° C. | 100% | 99% | 98% | 94% | 88% | 99% | 100% | 95% |
| 37° C. | 100% | 92% | 94% | 92% | 90% | 91% | 47% | 79% |
| 40° C. | 100% | 90% | 83% | 77% | 75% | 83% | 82% | 73% |
| 45° C. | 100% | 85% | 78% | 77% | 60% | 57% | 47% | 19% |
| 50° C. | 100% | 84% | 30% | 36% | 13% | 12% | 10% | 0% |

Example 6: Determining the pH Stability

The pH stability of the activated alcohol dehydrogenase of SEQ ID no. 1 was determined over a range from pH 4.0 to pH 10.0. To do this, a tenfold concentration of the activated alcohol dehydrogenase (100 nM) was stored in 10% Teorell Stenhagen buffer pH 4.0 to pH 10.0 for up to 120 minutes at a temperature of 30° C. After 0, 60, and 120 minutes, an aliquot of the alcohol dehydrogenase was taken and the activity in a transformation assay was determined, and as described in Example 3, carried out at 30° C. with the following components: 100 mM Tris-HCl, pH 7.5, 1 mM PMS, 50 ppm DON, 10 nM activated alcohol dehydrogenases of SEQ ID no. 1. The sampling to determine the activity was taken after 0, 10, 20, 30, and 40 min. The course of the DON reduction was determined for each pH value for each time. To determine the stability, the slope of the linear range of the DON transformation line was calculated for each pH value at the respective time. The slope of the linear range of the DON transformation line of the respective pH value at the time of t=0 min was used as the reference value for the calculation of the activities of the following incubation times. Table 7 shows the pH value, the time of the pH incubation in minutes, and the associated residual activities in percent. The alcohol dehydrogenase of SEQ ID no. 1 was stable at pH 5.0 to pH 9.0 after a 60-minute incubation. Surprisingly, the alcohol dehydrogenase exhibited particularly good stability in an acidic environment (no activity loss at pH 5.0) and in a heavily alkaline environment (no activity loss in an incubation after 120 min at pH 9.0).

TABLE 7

| | Incubation time | |
|---|---|---|
| | 60 min | 120 min |
| pH 4.0 | 72% | 51% |
| pH 5.0 | 111% | 109% |
| pH 6.0 | 92% | 88% |
| pH 7.0 | 87% | 85% |
| pH 8.0 | 83% | 73% |
| pH 9.0 | 93% | 60% |
| pH 10.0 | 69% | 55% |

Example 7: Transformation of DON in Complex Matrices

To determine the capability of the activated alcohol dehydrogenases to transform trichothecenes in complex matrices also without an external addition of synthetic redox cofactors, the activated alcohol dehydrogenase of SEQ ID no. 1 was produced as described in Example 3, and DON transformation assays were carried out in complex matrices. Here, complex matrices are defined as the rumen fluid of cattle, intestinal contents from the jejunum of swine, gastric juice of swine, saliva of humans and swine, granulated piglet feed, and granulated piglet feed mixed with saliva, rumen fluid, or intestine contents, among other things. In order to have a comparison with the buffer system, inspections were carried out with Tris-HCl, as described in Example 3. For the piglet feed, a standard feed based on maize, soya, and barley was used.

To determine the alcohol dehydrogenase activity in rumen fluid (pH 5.9), 1 ml of sterile rumen fluid filtrate was added to 100, 200, and 300 nM of activated alcohol dehydrogenase of SEQ ID no. 1 and 50 ppm DON in each case. The control batches were tested in aqueous solution, as described in Example 3. The transformation assays were incubated at 30° C. in a thermoblock for up to 24 hours. Samples were taken after 0, 0.5, 1.0, 5.0, and 24.0 hours, in which case a 0.1 ml sample was taken at each time, and the reaction was stopped with 0.1 ml methanol. The samples were stored at −20° C., defrosted, and centrifuged for 10 min at 13,000 rpm with an Eppendorf tabletop centrifuge, and filtered sterilely with a 0.2 µM Spartan filter. For the LC-MS/MS, the samples were diluted as described in Example 3 and analysed by means of LC-MS/MS. The concentration of DON at the time of t=0 h was used as the reference value (100%) for the following values. Table 8 shows the percentage of DON concentration that was measured at a certain time relative to the time of t=0 h. For the activity in the Tris-HCl buffer, the presence of an externally added synthetic redox cofactor is necessary, because the transformation of DON occurs slowly, and was detectable only 24 hours later with an alcohol dehydrogenase concentration of 300 nM. Surprisingly, it has been demonstrated that DON is transformed without the addition of an external synthetic redox cofactor in a sterile rumen fluid filtrate at a pH value of 5.9. This shows clearly that there are substances in the rumen fluid that serve as natural redox cofactors. With a concentration of 300 nM, only 42% of the initial DON quantity is contained in the preparation after 5 hours incubation. After 24 hours incubation, DON is detectable only in low quantities with an alcohol dehydrogenase concentration greater than 200 nM.

TABLE 8

|  | Rumen fluid with synthetic redox cofactor | Rumen fluid without synthetic redox cofactor | | | Tris-HCl pH 7.5 without synthetic redox cofactor | | |
| --- | --- | --- | --- | --- | --- | --- | --- |
|  | 100 nM | 100 nM | 200 nM | 300 nM | 100 nM | 200 nM | 300 nM |
| 0 h | 100% | 100% | 100% | 100% | 100% | 100% | 100% |
| 0.5 h | 0% | 100% | 100% | 87% | 100% | 99% | 95% |
| 1.0 h | 0% | 100% | 100% | 83% | 100% | 99% | 89% |
| 5.0 h | 0% | 94% | 75% | 42% | 99% | 88% | 86% |
| 24.0 h | 0% | 53% | 3% | 0% | 97% | 84% | 67% |

To determine the alcohol dehydrogenase activity in swine gastric juice without mash with a pH value of about 3, in swine intestinal contents with a pH value of about 6, and in swine and human saliva, 300 nM activated alcohol dehydrogenase SEQ ID no. 1, about 20 ppm DON, was mixed with 1 ml gastric juice (sterilely filtered), 1 ml mushy intestinal contents, or 1 ml saliva in each case. As a negative check, assays containing only digestion fluids with 20 ppm DON were included, and as a positive check, transformation assays containing all the components, including 20 mM of the synthetic redox cofactor PFC (III), were used. Samples were taken after 0, 3.0, 5.0, and 24.0 hours, in which case a 0.1 ml sample was taken at each time, and the reaction was stopped with 0.1 ml methanol. The samples were stored at 20° C., defrosted, and centrifuged for 10 min at 13,000 rpm with an Eppendorf tabletop centrifuge, and filtered sterilely (0.2 µM Spartan filter). For the LC-MS/MS, the samples were diluted 1:10 in the eluant (see Example 3) and analysed by means of LC-MS/MS as in Example 3. Table 9 shows the respective DON concentrations that were measured at the time of the sampling. Surprisingly, a reduction of DON in the saliva occurred without an externally added synthetic redox cofactor (regardless of the species). This shows clearly that there are substances in the saliva secretions of humans and swine that are suitable as natural redox cofactors for the transformation of DON with the alcohol dehydrogenase SEQ ID no. 1. No substantial reduction of the DON concentration was measured in the pure gastric juice without mush. A reduction of the DON concentration occurred in the intestinal contents only by adding the synthetic redox cofactor.

TABLE 9

|  |  | DON [ppm] | | | |
| --- | --- | --- | --- | --- | --- |
| Sample |  | 0 h | 3 h | 5 h | 24 h |
| Saliva (human) | Negative check | 20 | 19 | 18 | 18 |
|  | 0 mM PFC (III) | 20 | 13 | 12 | 8 |
|  | Positive check 20 mM PFC (III) | 18 | 0 | 0 | 0 |
| Saliva (swine) | Negative check | 20 | 20 | 19 | 18 |
|  | 0 mM PFC (III) | 21 | 10 | 8 | 5 |
|  | Positive check 20 mM PFC (III) | 20 | 0 | 0 | 0 |
| Gastric juice | Negative check | 22 | 22 | 21 | 21 |
|  | 0 mM PFC (III) | 22 | 21 | 21 | 20 |
|  | Positive check 20 mM PFC (III) | 24 | 21 | 19 | 18 |
| Intestinal contents | Negative check | 21 | 20 | 20 | 20 |
|  | 0 mM PFC (III) | 24 | 23 | 22 | 22 |
|  | Positive check 20 mM PFC (III) | 23 | 9 | 8 | 4 |

To determine the activity of the alcohol dehydrogenases in piglet feed, 100 mg of piglet feed was mixed with 400 µl 100 mM Tris-HCl buffer, pH 7.5, 400 µl swine saliva, 400 µl sterile swine gastric juice or 400 µl swine intestinal contents respectively. These piglet feed suspensions were stored overnight at 4° C. Following this, about 20 ppm DON, and/or 300 nM activated alcohol dehydrogenases of SEQ ID no. 1, and/or 20 mM of the synthetic redox cofactor PFC (III) were added to all the samples. The preparations without alcohol dehydrogenase and without the external synthetic redox cofactor were used as the negative check. The preparations with the added alcohol dehydrogenase and synthetic redox cofactor were used as the positive check. Samples were taken after 0, 3.0, 5.0, and 24.0 hours. One entire sample was used each time. For the sample, 500 µl methanol was added, followed by 30 min homogenization on a shaker with 300 rpm. Following this, the samples were centrifuged for 15 min (Eppendorf tabletop centrifuge, 13,000 rpm) and the supernatant was filtered with a syringe through a 0.2 µM Spartan filter. The supernatants were stored at −20° C., defrosted, and for the LC-MS/MS diluted 1:10 in the eluant, and analysed by means of LC-MS/MS as described in Example 3.

Table 10 shows the DON concentration that was present in the samples at the respective times. In the piglet feed buffer mixture there were substances that can assume the role of the externally added synthetic redox cofactors, because the DON concentration decreases continuously in the absence of the external synthetic redox cofactor. These substances come from the piglet feed, because as shown before, no DON transformation could be measured in the buffer without an external synthetic redox cofactor. In the presence of the external synthetic redox cofactor, the transformation of DON in the piglet feed buffer mixture occurs faster in comparison.

In the mixture of piglet feed and saliva, the alcohol dehydrogenase also exhibited activity independently of the presence of the external synthetic redox cofactor; whereas a faster reduction of DON occurred in the transformation assays that contained the external synthetic redox cofactor.

Surprisingly, the alcohol dehydrogenase of SEQ ID no. 1 in the piglet feed mixture is also active without adding the external synthetic redox cofactor. By adding piglet feed to the gastric juice, on the one hand, the pH of the gastric juice was increased, and on the other hand, naturally occurring redox cofactors that can replace the external synthetic redox cofactor were released from the piglet feed. Activity of the alcohol dehydrogenase was ascertained in the intestinal contents only when an external synthetic redox cofactor was added to the transformation assay.

TABLE 10

|  |  | DON [ppm] | | | |
|---|---|---|---|---|---|
| Sample | | 0 h | 3 h | 5 h | 24 h |
| Piglet feed in buffer | Negative check | 21 | 20 | 20 | 20 |
|  | 0 mM PFC (III) | 20 | 10 | 9 | 5 |
|  | Positive check 20 mM PFC (III) | 21 | 0 | 0 | 0 |
| Piglet feed in saliva | Negative check | 20 | 20 | 20 | 20 |
|  | 0 mM PFC (III) | 20 | 12 | 9 | 8 |
|  | Positive check 20 mM PFC (III) | 21 | 1 | 0.8 | 0.5 |
| Piglet feed in gastric juice | Negative check | 21 | 21 | 20 | 20 |
|  | 0 mM PFC (III) | 20 | 7 | 5 | 2 |
|  | Positive check 20 mM PFC (III) | 20 | 5 | 0.7 | 0 |
| Piglet feed in intestinal contents | Negative check | 21 | 20 | 20 | 20 |
|  | 0 mM PFC (III) | 21 | 20 | 18 | 16 |
|  | Positive check 20 mM PFC (III) | 20 | 5 | 3 | 0.7 |

---

The invention claimed is:

1. A method for the enzymatic transformation of trichothecenes, wherein at least one trichothecene exhibiting a hydroxyl group on the C-3 atom is brought into contact with an alcohol dehydrogenase of sequence ID numbers 2, 3 or 4 containing metal ions and a quinone cofactor, or with a functional variant thereof having a sequence identity of at least 99% thereto, with at least one redox cofactor and water, and if necessary at least one excipient.

2. The method according to claim 1, wherein the trichothecene exhibiting a hydroxyl group on the C-3 atom is transformed at a temperature between 5° C. and 55° C.

3. The method according to claim 1, wherein at least one trichothecene exhibiting a hydroxyl group on the C-3 atom is brought into contact with the alcohol dehydrogenase containing metal ions and a quinone cofactor, or at least a functional variant thereof, with the redox factor, with water, and if necessary, with the excipient, for at least one minute.

4. The method according to claim 1, wherein the quinone cofactor is selected from the group pyrroloquinoline quinone (PCC), tryptophan tryptophylquinone (TTC), topaquinone (TPC), lysine tyrosylquinone (LTC), and cysteine tryptophylquinone (CTC).

5. The method according to claim 1, wherein the quinone cofactor is bound to the alcohol dehydrogenase by at least one metal ion selected from the group $Li^+$, $Na^+$, $K^+$, $Mg^{2+}$, $Ca^{2+}$, $Zn^{2+}$, $Zn^{3+}$, $Mn^{2+}$, $Mn^{3+}$, $Fe^{2+}$, $Fe^{3+}$, $Cu^{2+}$, $Cu^{3+}$, $Co^{2+}$ and $Co^{3+}$.

6. The method according to claim 1, wherein the at least one redox cofactor is selected from the group phenazine methosulphate (PMS), PMS derivatives, potassium hexacyanoferrate (III), sodium hexacyanoferrate (III), cytochrome C, coenzyme Q1, coenzyme Q10, methylene blue, and N,N,N',N'-tetramethyl-p-phenylenediamine (TMPD).

* * * * *

SEQUENCE LISTING

```
<160> NUMBER OF SEQ ID NOS: 4

<210> SEQ ID NO 1
<211> LENGTH: 608
<212> TYPE: PRT
<213> ORGANISM: Pseudogluconobacter sp.

<400> SEQUENCE: 1

Met Arg Phe Glu Tyr Leu Arg Gln Asn Val Val Gly Leu Ala Leu Ser
1               5                   10                  15

Thr Ala Leu Ile Ala Ser Leu Ser Gly Pro Ala Phe Ala Gln His Asp
            20                  25                  30

Ala Asn Ala Ala Ala Glu Pro Ser Lys Ala Gly Gln Ser Ala Ile Glu
        35                  40                  45

Asn Phe Gln Pro Val Thr Ala Asp Asp Leu Ala Gly Lys Asn Pro Ala
    50                  55                  60

Asn Trp Pro Ile Leu Arg Gly Asn Tyr Gln Gly Trp Gly Tyr Ser Pro
65                  70                  75                  80

Leu Asp Gln Ile Asn Lys Asp Asn Val Gly Asp Leu Gln Leu Val Trp
                85                  90                  95

Ser Arg Thr Met Glu Pro Gly Ser Asn Glu Gly Ala Ala Ile Ala Tyr
            100                 105                 110

Asn Gly Val Ile Phe Leu Gly Asn Thr Asn Asp Val Ile Gln Ala Ile
        115                 120                 125

Asp Gly Lys Thr Gly Ser Leu Ile Trp Glu Tyr Arg Arg Lys Leu Pro
    130                 135                 140

Ser Ala Ser Lys Phe Ile Asn Ser Leu Gly Ala Ala Lys Arg Ser Ile
145                 150                 155                 160

Ala Leu Phe Gly Asp Lys Val Tyr Phe Val Ser Trp Asp Asn Phe Val
                165                 170                 175

Val Ala Leu Asp Ala Lys Thr Gly Lys Leu Ala Trp Glu Thr Asn Arg
            180                 185                 190

Gly Gln Gly Val Glu Glu Gly Val Ala Asn Ser Ser Gly Pro Ile Val
        195                 200                 205

Val Asp Gly Val Val Ile Ala Gly Ser Thr Cys Gln Phe Ser Gly Phe
    210                 215                 220
```

```
Gly Cys Tyr Val Thr Gly Thr Asp Ala Glu Ser Gly Glu Glu Leu Trp
225                 230                 235                 240

Arg Asn Thr Phe Ile Pro Arg Pro Gly Glu Glu Gly Asp Asp Thr Trp
                245                 250                 255

Gly Gly Ala Pro Tyr Glu Asn Arg Trp Met Thr Gly Ala Trp Gly Gln
            260                 265                 270

Ile Thr Tyr Asp Pro Glu Leu Asp Leu Val Tyr Tyr Gly Ser Thr Gly
        275                 280                 285

Ala Gly Pro Ala Ser Glu Val Gln Arg Gly Thr Glu Gly Gly Thr Leu
    290                 295                 300

Ala Gly Thr Asn Thr Arg Phe Ala Val Lys Pro Lys Thr Gly Glu Val
305                 310                 315                 320

Val Trp Lys His Gln Thr Leu Pro Arg Asp Asn Trp Asp Ser Glu Cys
                325                 330                 335

Thr Phe Glu Met Met Val Val Ser Thr Ser Val Asn Pro Asp Ala Lys
            340                 345                 350

Ala Asp Gly Met Met Ser Val Gly Ala Asn Val Pro Arg Gly Glu Thr
        355                 360                 365

Arg Lys Val Leu Thr Gly Val Pro Cys Lys Thr Gly Val Ala Trp Gln
370                 375                 380

Phe Asp Ala Lys Thr Gly Asp Tyr Phe Trp Ser Lys Ala Thr Val Glu
385                 390                 395                 400

Gln Asn Ser Ile Ala Ser Ile Asp Asp Thr Gly Leu Val Thr Val Asn
            405                 410                 415

Glu Asp Met Ile Leu Lys Glu Pro Gly Lys Thr Tyr Asn Tyr Cys Pro
        420                 425                 430

Thr Phe Leu Gly Gly Arg Asp Trp Pro Ser Ala Gly Tyr Leu Pro Lys
    435                 440                 445

Ser Asn Leu Tyr Val Ile Pro Leu Ser Asn Ala Cys Tyr Asp Val Met
    450                 455                 460

Ala Arg Thr Thr Glu Ala Thr Pro Ala Asp Val Tyr Asn Thr Asp Ala
465                 470                 475                 480

Thr Leu Val Leu Ala Pro Gly Lys Thr Asn Met Gly Arg Val Asp Ala
            485                 490                 495

Ile Asp Leu Ala Thr Gly Glu Thr Lys Trp Ser Tyr Glu Thr Arg Ala
        500                 505                 510

Ala Leu Tyr Asp Pro Val Leu Thr Thr Gly Gly Asp Leu Val Phe Val
    515                 520                 525

Gly Gly Ile Asp Arg Asp Phe Arg Ala Leu Asp Ala Glu Ser Gly Lys
    530                 535                 540

Glu Val Trp Ser Thr Arg Leu Pro Gly Ala Val Ser Gly Tyr Thr Thr
545                 550                 555                 560

Ser Tyr Ser Ile Asp Gly Arg Gln Tyr Val Ala Val Ser Gly Gly
            565                 570                 575

Ser Leu Gly Gly Pro Thr Phe Gly Pro Thr Thr Pro Asp Val Asp Ser
        580                 585                 590

Ala Ser Gly Ala Asn Gly Ile Tyr Val Phe Ala Leu Pro Glu Lys Lys
    595                 600                 605

<210> SEQ ID NO 2
<211> LENGTH: 586
<212> TYPE: PRT
<213> ORGANISM: Devosia sp.
```

```
<400> SEQUENCE: 2

Met Ser Ala Pro Ala Phe Ala Gln His Ala Asp Gly Ala Ala Glu
1               5                   10                  15

Thr Ala Ala Pro Gly Gln Ser Ala Ile Glu Asn Phe Gln Pro Val Thr
            20                  25                  30

Ala Glu Asp Leu Ala Gly Gly Asn Ala Ala Asn Trp Pro Ile Leu Arg
        35                  40                  45

Gly Asn Tyr Gln Gly Trp Gly Tyr Thr Gln Leu Asp Gln Ile Asn Lys
    50                  55                  60

Asp Asn Val Gly Gln Leu Gln Leu Ala Trp Ala Arg Thr Met Glu Pro
65                  70                  75                  80

Gly Ser Asn Glu Gly Ser Ala Ile Ala Tyr Asn Gly Val Val Phe Leu
                85                  90                  95

Gly Asn Ala Asn Asp Val Val Gln Ala Ile Asp Gly Lys Thr Gly Asn
            100                 105                 110

Leu Ile Trp Glu Tyr Arg Arg Lys Leu Pro Pro Ala Ser Lys Phe Ile
        115                 120                 125

Asn Ser Leu Gly Ala Ala Lys Arg Ser Ile Ala Leu Phe Gly Asp Lys
    130                 135                 140

Val Tyr Phe Val Ser Trp Asp Asn Phe Val Val Ala Leu Asp Ala Lys
145                 150                 155                 160

Thr Gly Lys Leu Ala Trp Glu Thr Asn Arg Gly Gln Gly Val Glu Glu
                165                 170                 175

Gly Val Ser Asn Ser Ser Gly Pro Ile Val Val Asp Gly Val Val Ile
            180                 185                 190

Ala Gly Ser Thr Cys Gln Tyr Ser Gly Phe Gly Cys Tyr Val Thr Gly
        195                 200                 205

Thr Asp Ala Glu Ser Gly Glu Glu Leu Trp Arg Asn Thr Phe Ile Pro
    210                 215                 220

Arg Pro Gly Glu Gly Asp Asp Thr Trp Gly Gly Ala Pro Tyr Glu
225                 230                 235                 240

Asn Arg Trp Met Thr Gly Ala Trp Gly Gln Ile Thr Tyr Asp Pro Glu
                245                 250                 255

Leu Asp Leu Val Tyr Tyr Gly Ser Thr Gly Ala Gly Pro Ala Ser Glu
            260                 265                 270

Val Gln Arg Gly Thr Glu Gly Thr Leu Ala Gly Thr Asn Thr Arg
        275                 280                 285

Phe Ala Val Lys Pro Lys Thr Gly Glu Val Val Trp Lys His Gln Thr
    290                 295                 300

Leu Pro Arg Asp Asn Trp Asp Ser Glu Cys Thr Phe Glu Met Met Val
305                 310                 315                 320

Val Ser Thr Thr Val Asn Pro Asp Ala Gly Ala Asp Gly Met Met Ser
                325                 330                 335

Val Gly Ala Asn Val Pro Arg Gly Glu Thr Arg Lys Val Leu Thr Gly
            340                 345                 350

Val Pro Cys Lys Thr Gly Val Ala Trp Gln Phe Asp Ala Glu Thr Gly
        355                 360                 365

Asp Tyr Phe Trp Ser Lys Ala Thr Val Glu Gln Asn Ser Ile Ala Ser
    370                 375                 380

Ile Asp Asp Lys Gly Leu Val Thr Val Asn Glu Asp Met Ile Leu Lys
385                 390                 395                 400

Glu Pro Gly Lys Asp Tyr Asn Tyr Cys Pro Thr Phe Leu Gly Gly Arg
                405                 410                 415
```

Asp Trp Pro Ser Ala Gly Tyr Leu Pro Lys Ser Asn Leu Tyr Val Ile
            420                 425                 430

Pro Leu Ser Asn Ala Cys Tyr Asp Leu Lys Ala Arg Thr Glu Ala
        435                 440                 445

Thr Pro Ala Asp Val Tyr Asn Thr Asp Ser Thr Val Lys Leu Ala Pro
    450                 455                 460

Gly Lys Thr Asn Met Gly Arg Val Asp Ala Ile Asp Val Ala Thr Gly
465                 470                 475                 480

Ala Thr Lys Trp Ser Phe Glu Thr Glu Ala Ala Leu Tyr Asp Pro Val
                485                 490                 495

Met Thr Thr Ala Gly Asp Leu Val Phe Val Gly Ser Thr Asp Arg Met
        500                 505                 510

Phe Arg Ala Leu Asp Ala Glu Thr Gly Lys Glu Val Trp Ser Thr Arg
    515                 520                 525

Leu Pro Gly Ala Ile Ser Gly Tyr Thr Thr Ser Tyr Ser Ile Asp Gly
    530                 535                 540

Arg Gln Tyr Val Ala Val Ala Gly Gly Ser Leu Gly Thr Gly Phe
545                 550                 555                 560

Phe Lys Ala Ala Val Pro Gly Val Asp Ala Val Gln Gly Gly Asn Gly
                565                 570                 575

Ile Tyr Val Phe Ala Leu Pro Glu Ala Lys
        580                 585

<210> SEQ ID NO 3
<211> LENGTH: 603
<212> TYPE: PRT
<213> ORGANISM: Devosia sp.

<400> SEQUENCE: 3

Met Arg Gln Asn Val Val Gly Leu Ala Leu Ser Thr Ala Leu Ile Ala
1               5                   10                  15

Ser Leu Ser Ala Pro Ala Phe Ala Gln His Ala Asp Gly Ala Ala Ala
            20                  25                  30

Glu Thr Ala Ala Pro Gly Gln Ser Ala Ile Glu Asn Phe Gln Pro Val
        35                  40                  45

Thr Ala Glu Asp Leu Ala Gly Gly Asn Ala Ala Asn Trp Pro Ile Leu
    50                  55                  60

Arg Gly Asn Tyr Gln Gly Trp Gly Tyr Thr Gln Leu Asp Gln Ile Asn
65                  70                  75                  80

Lys Asp Asn Val Gly Gln Leu Gln Leu Ala Trp Ala Arg Thr Met Glu
                85                  90                  95

Pro Gly Ser Asn Glu Gly Ser Ala Ile Ala Tyr Asn Gly Val Val Phe
            100                 105                 110

Leu Gly Asn Ala Asn Asp Val Val Gln Ala Ile Asp Gly Lys Thr Gly
        115                 120                 125

Asn Leu Ile Trp Glu Tyr Arg Arg Lys Leu Pro Pro Ala Ser Lys Phe
    130                 135                 140

Ile Asn Ser Leu Gly Ala Ala Lys Arg Ser Ile Ala Leu Phe Gly Asp
145                 150                 155                 160

Lys Val Tyr Phe Val Ser Trp Asp Asn Phe Val Ala Leu Asp Ala
                165                 170                 175

Lys Thr Gly Lys Leu Ala Trp Glu Thr Asn Arg Gly Gln Gly Val Glu
            180                 185                 190

Glu Gly Val Ser Asn Ser Ser Gly Pro Ile Val Val Asp Gly Val Val

```
            195                 200                 205
Ile Ala Gly Ser Thr Cys Gln Tyr Ser Gly Phe Gly Cys Tyr Val Thr
210                 215                 220

Gly Thr Asp Ala Glu Ser Gly Glu Glu Leu Trp Arg Asn Thr Phe Ile
225                 230                 235                 240

Pro Arg Pro Gly Glu Glu Asp Thr Trp Gly Ala Pro Tyr
                245                 250                 255

Glu Asn Arg Trp Met Thr Gly Ala Trp Gly Gln Ile Thr Tyr Asp Pro
                260                 265                 270

Glu Leu Asp Leu Val Tyr Tyr Gly Ser Thr Gly Ala Gly Pro Ala Ser
            275                 280                 285

Glu Val Gln Arg Gly Thr Glu Gly Gly Thr Leu Ala Gly Thr Asn Thr
290                 295                 300

Arg Phe Ala Val Lys Pro Lys Thr Gly Glu Val Val Trp Lys His Gln
305                 310                 315                 320

Thr Leu Pro Arg Asp Asn Trp Asp Ser Glu Cys Thr Phe Glu Met Met
                325                 330                 335

Val Val Ser Thr Thr Val Asn Pro Asp Ala Gly Ala Asp Gly Met Met
            340                 345                 350

Ser Val Gly Ala Asn Val Pro Arg Gly Glu Thr Arg Lys Val Leu Thr
            355                 360                 365

Gly Val Pro Cys Lys Thr Gly Val Ala Trp Gln Phe Asp Ala Glu Thr
370                 375                 380

Gly Asp Tyr Phe Trp Ser Lys Ala Thr Val Glu Gln Asn Ser Ile Ala
385                 390                 395                 400

Ser Ile Asp Asp Lys Gly Leu Val Thr Val Asn Glu Asp Met Ile Leu
                405                 410                 415

Lys Glu Pro Gly Lys Asp Tyr Asn Tyr Cys Pro Thr Phe Leu Gly Gly
                420                 425                 430

Arg Asp Trp Pro Ser Ala Gly Tyr Leu Pro Lys Ser Asn Leu Tyr Val
            435                 440                 445

Ile Pro Leu Ser Asn Ala Cys Tyr Asp Leu Lys Ala Arg Thr Thr Glu
450                 455                 460

Ala Thr Pro Ala Asp Val Tyr Asn Thr Asp Ser Thr Val Lys Leu Ala
465                 470                 475                 480

Pro Gly Lys Thr Asn Met Gly Arg Val Asp Ala Ile Asp Val Ala Thr
                485                 490                 495

Gly Ala Thr Lys Trp Ser Phe Glu Thr Glu Ala Ala Leu Tyr Asp Pro
            500                 505                 510

Val Met Thr Thr Ala Gly Asp Leu Val Phe Val Gly Ser Thr Asp Arg
515                 520                 525

Met Phe Arg Ala Leu Asp Ala Glu Thr Gly Lys Glu Val Trp Ser Thr
                530                 535                 540

Arg Leu Pro Gly Ala Ile Ser Gly Tyr Thr Thr Ser Tyr Ser Ile Asp
545                 550                 555                 560

Gly Arg Gln Tyr Val Ala Val Ala Gly Gly Ser Leu Gly Thr Gly
                565                 570                 575

Phe Phe Lys Ala Ala Val Pro Gly Val Asp Ala Val Gln Gly Gly Asn
            580                 585                 590

Gly Ile Tyr Val Phe Ala Leu Pro Glu Ala Lys
            595                 600
```

<210> SEQ ID NO 4

```
<211> LENGTH: 609
<212> TYPE: PRT
<213> ORGANISM: Devosia sp.

<400> SEQUENCE: 4
```

| | | | | | | | | | | | | | | | |
|---|---|---|---|---|---|---|---|---|---|---|---|---|---|---|---|
|Met|Arg|Phe|Glu|Cys|Ile|Arg|Gln|Asn|Ala|Val|Gly|Leu|Ala|Leu|Ser|
|1| | | |5| | | | |10| | | | |15| |
|Thr|Ala|Leu|Ile|Ala|Ser|Leu|Ser|Ala|Pro|Ala|Phe|Ala|Gln|His|Ala|
| | | |20| | | | |25| | | | |30| | |
|Asp|Gly|Ala|Ala|Thr|Glu|Ala|Val|Ser|Ala|Gln|Ser|Ala|Ile|Glu|Asn|
| | | |35| | | | |40| | | | |45| | |
|Phe|Lys|Pro|Val|Thr|Ala|Glu|Asp|Ile|Ala|Gly|Ala|Asn|Ser|Ala|Asn|
|50| | | | |55| | | | |60| | | | | |
|Trp|Pro|Ile|Leu|Arg|Gly|Asn|Tyr|Asn|Gly|Trp|Gly|Tyr|Thr|Pro|Leu|
|65| | | | |70| | | | |75| | | | |80|
|Asp|Gln|Ile|Asn|Lys|Asp|Asn|Val|Gly|Gln|Leu|Gln|Leu|Ala|Trp|Ser|
| | | | |85| | | | |90| | | | |95| |
|Arg|Thr|Met|Glu|Pro|Gly|Ser|Asn|Glu|Gly|Ala|Ala|Ile|Ala|Tyr|Asn|
| | | |100| | | | |105| | | | |110| | |
|Gly|Val|Val|Tyr|Leu|Gly|Asn|Ala|Asn|Asp|Val|Ile|Gln|Ala|Ile|Asp|
| | | |115| | | | |120| | | | |125| | |
|Gly|Lys|Thr|Gly|Asp|Leu|Ile|Trp|Glu|Tyr|Arg|Arg|Lys|Leu|Pro|Pro|
| |130| | | | |135| | | | |140| | | | |
|Ala|Ser|Lys|Phe|Ile|Asn|Ser|Leu|Gly|Gln|Ala|Lys|Arg|Ser|Ile|Ala|
|145| | | | |150| | | | |155| | | | |160|
|Leu|Phe|Gly|Asp|Lys|Val|Tyr|Phe|Val|Ser|Trp|Asp|Asn|Phe|Val|Ala|
| | | | |165| | | | |170| | | | |175| |
|Ala|Leu|Asp|Ala|Lys|Thr|Gly|Lys|Leu|Ala|Trp|Glu|Thr|Asn|Arg|Gly|
| | | |180| | | | |185| | | | |190| | |
|Gln|Gly|Val|Asp|Glu|Gly|Val|Ser|Asn|Ser|Ser|Gly|Pro|Ile|Val|Val|
| | | |195| | | | |200| | | | |205| | |
|Asp|Gly|Val|Val|Ile|Ala|Gly|Thr|Thr|Cys|Gln|Phe|Ser|Gly|Phe|Gly|
| |210| | | | |215| | | | |220| | | | |
|Cys|Tyr|Val|Thr|Gly|Thr|Asp|Ala|Glu|Ser|Gly|Glu|Glu|Leu|Trp|Arg|
|225| | | | |230| | | | |235| | | | |240|
|Asn|Thr|Phe|Ile|Pro|Arg|Pro|Gly|Glu|Glu|Gly|Asp|Asp|Thr|Trp|Gly|
| | | | |245| | | | |250| | | | |255| |
|Gly|Ala|Pro|Tyr|Glu|Asn|Arg|Trp|Met|Thr|Gly|Ala|Trp|Gly|Gln|Ile|
| | | |260| | | | |265| | | | |270| | |
|Thr|Tyr|Asp|Pro|Glu|Leu|Asp|Leu|Val|Tyr|Tyr|Gly|Ser|Thr|Gly|Ala|
| | | |275| | | | |280| | | | |285| | |
|Gly|Pro|Ala|Ser|Glu|Val|Gln|Arg|Gly|Thr|Glu|Gly|Gly|Thr|Leu|Ala|
| |290| | | | |295| | | | |300| | | | |
|Gly|Thr|Asn|Thr|Arg|Phe|Ala|Val|Lys|Pro|Lys|Thr|Gly|Glu|Val|Val|
|305| | | | |310| | | | |315| | | | |320|
|Trp|Lys|His|Gln|Thr|Leu|Pro|Arg|Asp|Asn|Trp|Asp|Gln|Glu|Cys|Thr|
| | | | |325| | | | |330| | | | |335| |
|Phe|Glu|Met|Met|Val|Val|Ser|Thr|Thr|Val|Asn|Pro|Asn|Ala|Asp|Ala|
| | | |340| | | | |345| | | | |350| | |
|Glu|Gly|Met|Phe|Ser|Val|Gly|Ala|Thr|Leu|Pro|Arg|Gly|Glu|Ser|Arg|
| | | |355| | | | |360| | | | |365| | |
|Lys|Val|Leu|Thr|Gly|Val|Pro|Cys|Lys|Thr|Gly|Val|Ala|Trp|Gln|Phe|
| |370| | | | |375| | | | |380| | | | |
|Asp|Ala|Glu|Thr|Gly|Asp|Tyr|Phe|Trp|Ser|Lys|Ala|Thr|Val|Ala|Gln|

-continued

```
385                 390                 395                 400
Asn Ala Val Ala Ser Ile Asp Asp Lys Gly Leu Val Thr Val Asn Glu
                405                 410                 415

Asp Met Ile Ile Lys Glu Pro Gly Lys Asn Tyr Glu Phe Cys Pro Thr
            420                 425                 430

Phe Leu Gly Gly Arg Asp Trp Pro Ser Ala Gly Tyr Leu Pro Ala Ser
        435                 440                 445

Asn Leu Tyr Val Ile Pro Leu Ser Gln Ala Cys Tyr Asp Leu Thr Ala
    450                 455                 460

Arg Thr Thr Glu Ala Thr Pro Ala Asp Val Tyr Asn Thr Asp Ala Thr
465                 470                 475                 480

Val Lys Leu Ala Pro Gly Arg Thr Asn Met Gly Arg Val Asp Ala Ile
                485                 490                 495

Asp Leu Ala Thr Gly Glu Thr Lys Trp Ser Phe Glu Thr Thr Ala Ala
            500                 505                 510

Leu Tyr Asp Pro Val Met Thr Thr Gly Gly Asp Leu Val Phe Val Gly
        515                 520                 525

Ser Thr Asp Arg Val Tyr Arg Ala Leu Asp Ala Ala Thr Gly Lys Glu
    530                 535                 540

Val Trp Ser Thr Arg Ile Pro Gly Ala Ile Ser Gly Phe Thr Thr Ser
545                 550                 555                 560

Tyr Ser Leu Asp Gly Arg Gln Tyr Val Ala Val Leu Ala Gly Gly Ser
                565                 570                 575

Leu Gly Thr Ser Phe Phe Lys Ala Ala Val Pro Asn Val Asp Ala Val
            580                 585                 590

Gln Gly Gly Asn Gly Ile Tyr Val Phe Ala Leu Pro Asp Ala Lys Ile
        595                 600                 605

Glu
```